United States Patent [19]

Brook

[11] Patent Number: 4,949,728
[45] Date of Patent: Aug. 21, 1990

[54] METHOD FOR PERFORMING IN VITRO DIAGNOSTIC TEST ON HORSES UTILIZING A BLOOD SAMPLE

[76] Inventor: Derek Brook, 20515 Covina Hills Rd., Covina, Calif. 91724

[21] Appl. No.: 277,983
[22] Filed: Nov. 30, 1988
[51] Int. Cl.⁵ .............................................. A61B 5/00
[52] U.S. Cl. .................................................. 128/760
[58] Field of Search ............... 128/760, 770, 303 R, 128/314, 315; 604/49

[56] References Cited

U.S. PATENT DOCUMENTS

| | | | |
|---|---|---|---|
| 3,898,982 | 8/1975 | Katsuda | 128/760 |
| 4,064,871 | 12/1977 | Reno | 128/314 |
| 4,628,929 | 12/1986 | Intengan et al. | 128/314 |
| 4,643,189 | 2/1987 | Mintz | 128/314 |
| 4,715,374 | 12/1987 | Maggio | 128/314 |

*Primary Examiner*—Max Hindenburg
*Attorney, Agent, or Firm*—William W. Haefliger

[57] ABSTRACT

A method for easily and safely obtaining a blood sample from a horse or other hoofed animal is disclosed. The process involves the steps of making a small incision in the coronary plexus at the back of a hoof; allowing a small amount of blood to flow from the incision; and then collecting a portion of the resulting blood with a capillary tube or other withdrawing device.

7 Claims, 1 Drawing Sheet

METHOD FOR PERFORMING IN VITRO DIAGNOSTIC TEST ON HORSES UTILIZING A BLOOD SAMPLE

BACKGROUND OF THE INVENTION

The field of this invention involves testing procedures of the type commonly used by animal owners, and more specifically the invention relates to a method for obtaining a blood sample from a horse or other hoofed animal for test procedures.

Recently a number of laboratory tests have been devised which may be easily carried out by a horse owner. In the past, blood samples have been obtained from a horse by inserting a hypodermic needle into the jugular vein. Most horse owners are reluctant to carry out this procedure and usually require a veterinarian to obtain such samples. Many testing procedures which can be carried out on a blood sample are so simple that they can be performed by the owner. Thus, the need for a veterinarian to obtain the blood sample greatly increases the cost of testing.

Many methods have been tried to obtain a blood sample from a horse. One such approach is to make a small incision in the tip of a horse's ear. The horse reacts to this as being uncomfortable and because most incision devices make a clicking noise, this often startles the horse or causes the horse to raise or turn its head. This makes sample collecting very difficult.

Another approach is to make an incision in the muzzle of the horse. This is uncomfortable for the horse and also unsatisfactory.

While in vitro tests can be performed utilizing a urine sample, such samples are difficult to obtain and the use of a blood sample is preferable. A better means for obtaining such blood samples is needed. Some of the tests which may be carried out on a blood sample include pregnancy testing, general health screening, pregnancy progesterone levels and foal immunoglobulin levels.

SUMMARY OF THE INVENTION

It is a major object of the present invention to provide a safe and easy method for obtaining a blood sample from a horse or other hoofed animal, and by persons possessing no particular medical skills.

This object is carried out by a process which includes the steps of making a small incision in the coronary plexus of one of the legs of the horse, or hoofed animal, and allowing a small amount of blood to flow from the incision. The sample is then collected from this small amount of blood. Preferably, the incision is made by a spring-activated surgical blade and the blood sample is collected as by a capillary tube.

Additional objects include employing an incision-making device of the type having a spring-activated blade, and the method includes placing that device on the coronary plexus and then activating the device so that the blade swiftly moves from the device into the coronary plexus, and then retracts into the device.

Typically there is hair on the coronary plexus, and extending generally downwardly; and the method includes placing the device on the hair and then activating the blade to cause its cutting edge to move along an arc in the general direction of hair lengthwise extent, to easily penetrate the hair mass.

These and other objects and advantages of the invention, as well as the details of an illustrative embodiment, will be more fully understood from the following specification and drawings, in which:

DRAWING DESCRIPTION

DETAILED DESCRIPTION

Figure 1:
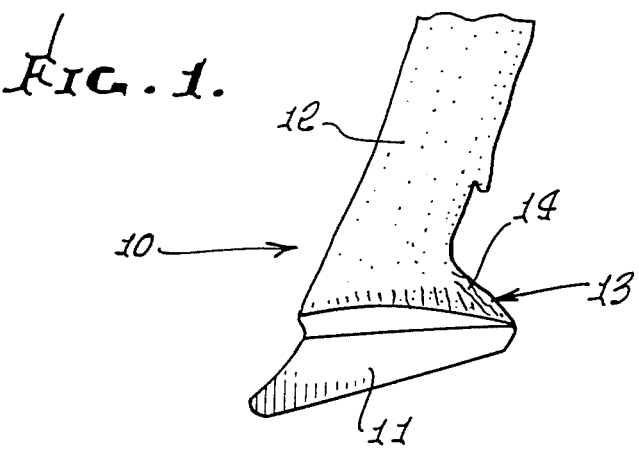
FIG. 1 is a perspective view of the left side and rear of the left front hoof of a horse.

The lower part of the front leg of a horse is shown in FIG. 1 in perspective view and indicated by reference character 10. Leg 10 has a hoof 11, a first phalanx 12 and a coronary plexus 13. The coronary plexus is a portion of a horse's leg which encircles the upper part of the hoof and covers the terminal part of the extensor tendon, the cartilage of the third phalanx and the bulbs of the digital cushion. The coronary plexus has numerous blood capillaries passing through it, since a source of blood is necessary for the nutrition of the hoof. The coronary plexus has relatively few nerve endings and may be cut without making the horse aware of such cut.

The process of the present invention includes the steps of making a small incision in the coronary plexus as indicated at reference character 14 of FIG. 1. Such incision may be easily made by an automatic incision making instrument of the type used for bleeding time determinations in humans. One such device is marketed by American Scientific Products under the Trademark, "SURGICUTT". This device has a pivoted razor blade which makes an incision about 5 mml. long and 1 mml. deep. Such device has been found to easily make an incision which provides a small drop of blood which may be readily collected.

Figure 2:
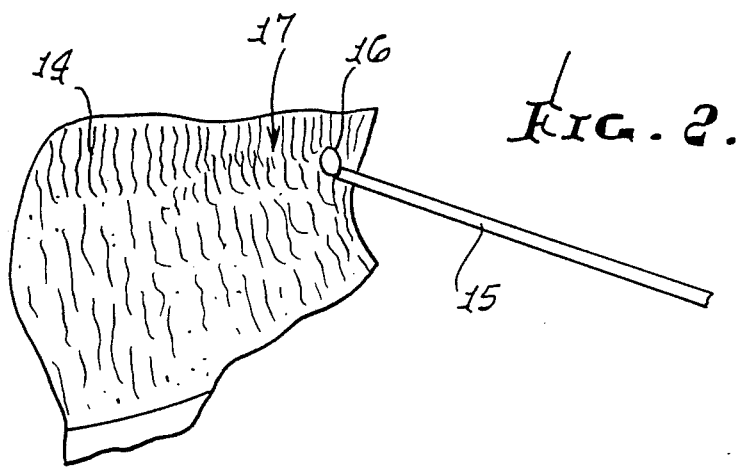
FIG. 2 is a perspective view of the hoof of FIG. 1 further including a sample collecting capillary tube.

One simple method of collecting a sample of blood is indicated in FIG. 2 where the tip of a sample-collecting capillary tube 15 is placed against the blood drop 16. The blood flows into the downwardly inclined capillary tube and may then be withdrawn and diluted for further testing. A 250yl capillary tube is appropriate, (one such tube is identified as a S/P Natelson Capillary Tube, Heparanized, Cat. #B3095-2). The sample may then be used for testing such as with a dip stick, with pads which change color with different concentrations of the targeted substance, or with testing machines.

While the cut may be made in any direction, it has been found that a generally vertical cut provides a larger blood sample than the horizontal cut and is preferred. Also, since hairs in the mass 17 extend downwardly, the device blade can easily penetrate between such hairs as while swinging along a vertical arc or moving in a vertical plane. Such hair can easily be cleaned, preliminarily, or a swatch removed to allow closer application of the device to the surface. While the sample can be taken from a hind leg, it is safer to withdraw the sample from one of the animal's front legs since the hind leg is a source of danger as from kicking. It is not necessary to lift the horse's leg and the sample may easily be taken as the horse is standing on the leg. This is an exceptionally safe procedure which causes no apparent discomfort to the horse; also, the wound heals readily.

Figure 3:
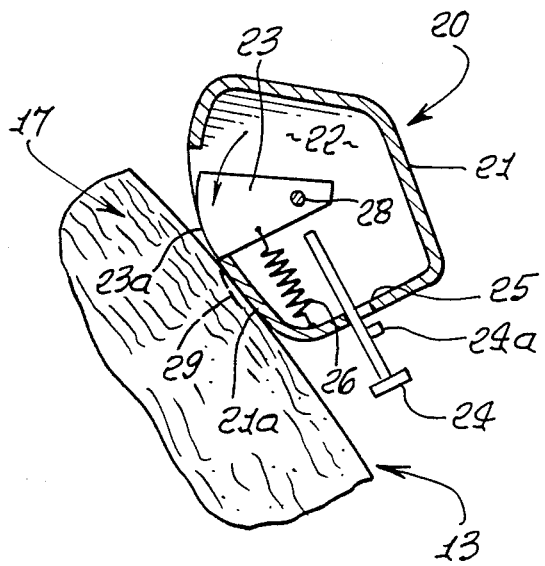
FIG. 3 is an enlarged view showing operation of an incision making device.

FIG. 3 diagrammatically shows an incision making device 20 of the type referred to. It has a case 21 with a hollow interior at 22. A blade 23 is pivoted at 28 to the case to swing in a vertical arc, when the case edge 21a is placed in a vertical plane, against the hair mass 17 on the coronary plexus. Pusher 24 is manipulable to push the blade upwardly to a "cocked" position, at which time a shoulder 24a on the pusher is held against a shoulder 25 of the case. This tensions a spring 26 which urges the blade downwardly. When the pusher shoulder 24a is tripped to dislodge it from shoulder 25, the tensioned spring quickly and suddenly urges the blade downwardly to swing in an arc, so that its edge 27a makes the shallow incision at 29, at which time a drop of blood then collects.

I claim:

1. A method for easily and safely obtaining a blood sample from a horse or other hoofed animal comprising the steps of:
   (a) making a small incision in the coronary plexus region of one of the legs of the horse or animal;
   (b) allowing a small amount of blood to flow from the incision; and
   (c) collecting a portion of the resulting blood sample,
   (d) said incision being made to a depth of about one millimeter, and along about five millimeters, while employing an incision-making device of the type having a case and a spring-activated blade, and the method including placing said device on said coronary plexus, while the horse is standing on the leg forming said coronary plexus, and then activating said device so that the blade swiftly moves relative to the case, to form the incision,
   (e) there being horse hair on said coronary plexus region, the hair extending lengthwise generally downwardly, said making of the incision being effected in the general direction of hair lengthwise extent.

2. The process of claim 1 wherein the coronary plexus of one of the front legs is used.

3. The process of claim 1 wherein the blade is moved about a pivot on said device, and the blade has a cutting edge which is moved along an arc.

4. The method of claim 3 including placing said device on the hair on said coronary plexus region and then activating the blade to cause said edge to move along an arc in the general direction of hair lengthwise extent.

5. The process of claim 1 wherein the collecting step includes employing a capillary tube to remove blood from the exterior of the coronary plexus.

6. The method of claim 1 including preliminarily cleaning said coronary plexus region.

7. The method of claim 1 including preliminarily removing hair from the coronary plexus region.

* * * * *